United States Patent
Castleberry et al.

(10) Patent No.: US 9,140,680 B2
(45) Date of Patent: Sep. 22, 2015

(54) METHOD FOR DETECTING WATER-IN-FUEL AFTER REFUELING EVENT

(71) Applicant: Ford Global Technologies, LLC, Dearborn, MI (US)

(72) Inventors: Larry Castleberry, Detroit, MI (US); Brien Lloyd Fulton, West Bloomfield, MI (US); Carlos Armesto, Canton, MI (US)

(73) Assignee: Ford Global Technologies, LLC, Dearborn, MI (US)

(*) Notice: Subject to any disclaimer, the term of this patent is extended or adjusted under 35 U.S.C. 154(b) by 191 days.

(21) Appl. No.: 13/932,684

(22) Filed: Jul. 1, 2013

(65) Prior Publication Data

US 2015/0006059 A1 Jan. 1, 2015

(51) Int. Cl.
*G01N 33/22* (2006.01)
*F02D 41/22* (2006.01)
*G01N 33/28* (2006.01)
*F02M 25/022* (2006.01)
*F02M 37/22* (2006.01)
*F02M 25/07* (2006.01)

(52) U.S. Cl.
CPC ............ *G01N 33/2835* (2013.01); *F02D 41/22* (2013.01); *F02M 25/0222* (2013.01); *F02M 25/0227* (2013.01); *F02M 25/0742* (2013.01); *F02M 37/221* (2013.01); *F02D 2041/224* (2013.01); *F02D 2200/0611* (2013.01); *F02M 25/0707* (2013.01)

(58) Field of Classification Search
CPC .............. F02D 41/22; F02D 2041/224; F02D 2200/0611; F02M 25/0222; F02M 25/0227; F02M 37/221; G01N 33/2835
See application file for complete search history.

(56) References Cited

U.S. PATENT DOCUMENTS

| 8,434,461 | B2* | 5/2013 | Kerns et al. | 123/521 |
| 8,464,513 | B2* | 6/2013 | Cooper et al. | 60/277 |
| 2011/0259088 | A1 | 10/2011 | Fisher et al. | |
| 2011/0265768 | A1* | 11/2011 | Kerns et al. | 123/521 |
| 2012/0023912 | A1* | 2/2012 | Cooper et al. | 60/277 |
| 2012/0042961 | A1* | 2/2012 | Anderson et al. | 137/172 |
| 2013/0144506 | A1* | 6/2013 | Nam | 701/102 |
| 2014/0081558 | A1* | 3/2014 | Fulton et al. | 701/108 |
| 2014/0166596 | A1* | 6/2014 | Anderson et al. | 210/799 |

FOREIGN PATENT DOCUMENTS

| CN | 102012388 A | 4/2011 |
| EP | 2290333 A1 | 3/2011 |

\* cited by examiner

*Primary Examiner* — Thomas Moulis
*Assistant Examiner* — Elizabeth Hadley
(74) *Attorney, Agent, or Firm* — James Dottavio; Alleman Hall McCoy Russell & Tuttle LLP

(57) ABSTRACT

A method, comprising generating a water-in-fuel indication responsive to a water-in-fuel content increasing more than a threshold amount within a threshold time of a refueling event is presented.

20 Claims, 6 Drawing Sheets

METHOD FOR DETECTING WATER-IN-FUEL AFTER REFUELING EVENT

BACKGROUND/SUMMARY

Water-in-fuel can cause corrosion and other damage to engine components such as fuel injection systems. As such, diesel engines typically employ a fuel/water separator to remove water from the fuel prior to fuel injection into the engine system. A water reservoir serves to collect the separated water from the fuel/water separator so that it can be manually drained at a suitable time such as when the engine is off, or automatically drained to the exhaust system under suitable conditions. Water reservoir sensors are used to determine when the reservoir levels are high and to trigger warning indicators to the vehicle operator signaling when reservoir draining is due.

Fisher et. al. (US 20110259088) describes a high water content fuel detection system where sensors determine a rate of accumulation of water in a water filter sump, which is monitored as an indication of the fuel quality. Depending on the sensor output, the system may request draining of the fuel filtration or fuel tank sump, and alert the operator of high water content fuel.

The inventors have recognized potential issues with the above system. Namely, conventional warning indicators only alert operators to high water reservoir levels or high water reservoir accumulation rates, and the operator has no way of knowing if the water capacity of the water separator reservoir has been exceeded. In particular, if a vehicle is refueled with high water content fuel, the risk of passing water to the fuel injection system is increased because water will immediately and steadily accumulate in the reservoir as fuel is consumed during vehicle operation. Accordingly, water can potentially be passed to the fuel injection system, resulting in degradation.

One approach which at least partially addresses the above issues is a method, comprising generating a water-in-fuel indication responsive to a water-in-fuel content increasing more than a threshold amount within a threshold time of a refueling event. In another embodiment, a method may comprise, responsive to a refueling condition and following completion of refueling, measuring a change in a water-in-fuel content, and generating a water-in-fuel operator indication if the change in the water-in-fuel content is greater than a non-zero threshold amount. In this manner, it may be possible to achieve the technical result of identifying a large increase in water volume in a short time interval following a refueling event and generate an operator warning to reduce degradation to the engine system.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
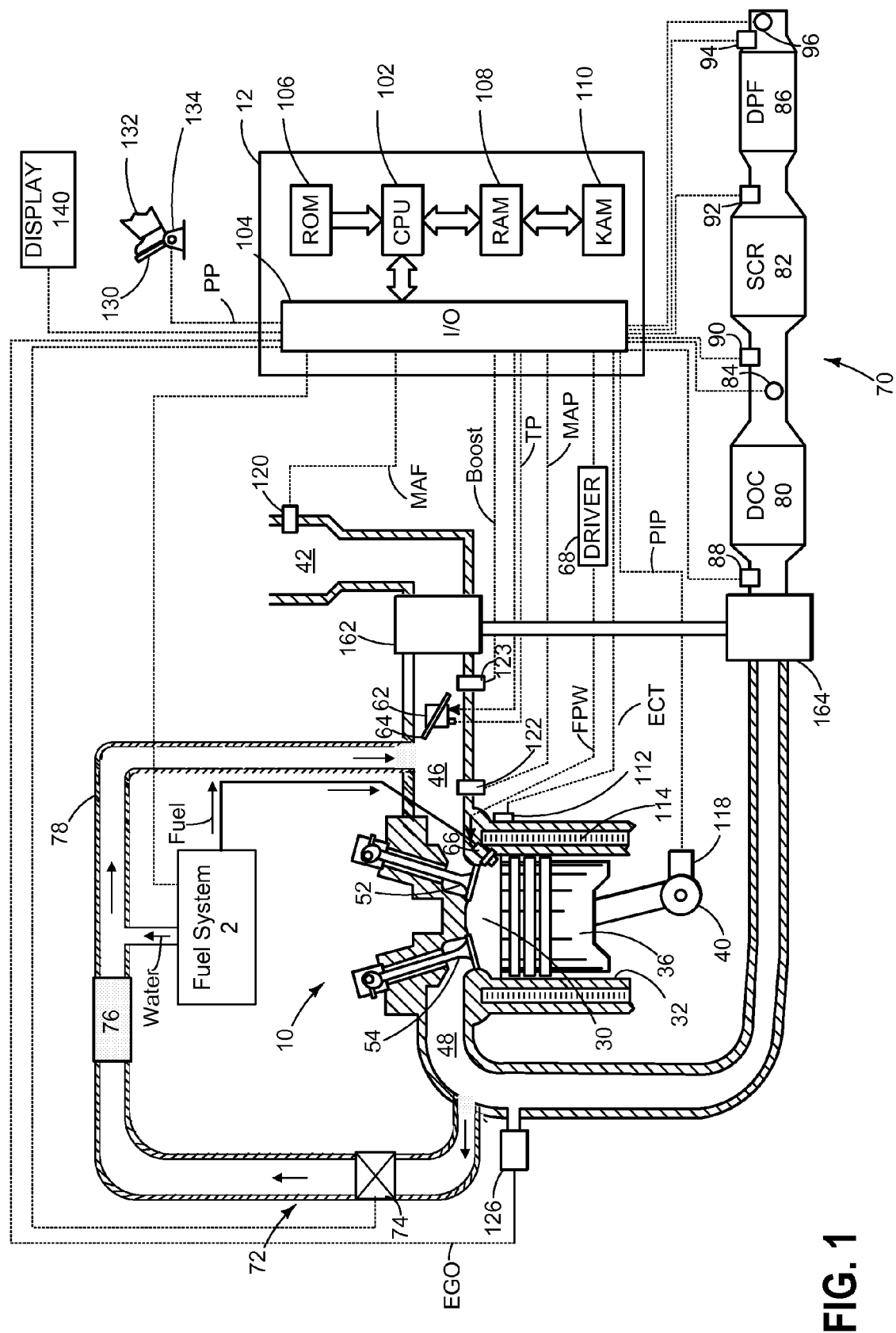
FIG. 1 is a schematic diagram of an example engine including an exhaust gas recirculation system, fuel system, and exhaust after-treatment system.
Figure 2:
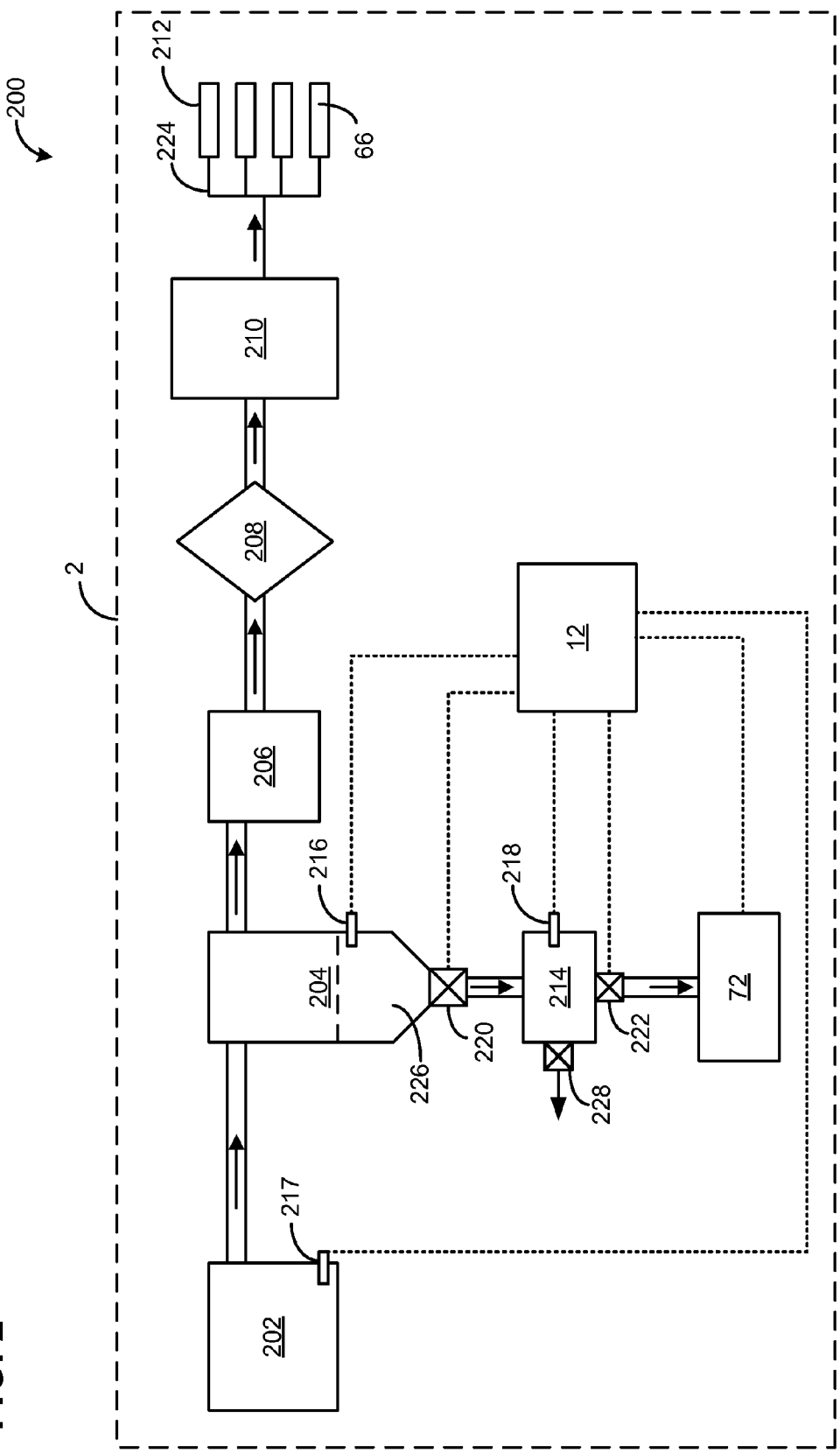
FIG. 2 is a schematic diagram of an example fuel system, including a fuel/water separator.

The following description relates to systems and methods for automatically draining water from a fuel/water separator into the exhaust gas recirculation (EGR) system for an engine, such as the engine shown in FIG. 1. Water filtered from a fuel/water separator in a fuel system, as shown in FIG. 2, may be collected in a water reservoir and then manually or automatically drained. A method generating a water-in-fuel indication responsive to a refueling event is illustrated in FIGS. 3, 4A, 4B, and 5. An example timeline illustrating a method of generating a water-in-fuel indication responsive to a refueling event is shown in FIG. 6.

Turning now to FIG. 1, a schematic diagram showing one cylinder of multi-cylinder engine 10, which may be included in a propulsion system of an automobile, is shown. Engine 10 may be controlled at least partially by a control system including controller 12 and by input from a vehicle operator 132 via an input device 130. In this example, input device 130 includes an accelerator pedal and a pedal position sensor 134 for generating a proportional pedal position signal PP. Combustion chamber (i.e., cylinder) 30 of engine 10 may include combustion chamber walls 32 with piston 36 positioned therein. Piston 36 may be coupled to crankshaft 40 so that reciprocating motion of the piston is translated into rotational motion of the crankshaft. Crankshaft 40 may be coupled to at least one drive wheel of a vehicle via an intermediate transmission system. Further, a starter motor may be coupled to crankshaft 40 via a flywheel to enable a starting operation of engine 10.

Combustion chamber 30 may receive intake air from intake manifold 46 via intake passage 42 and may exhaust combustion gases via exhaust passage 48. Intake manifold 46 and exhaust passage 48 can selectively communicate with combustion chamber 30 via respective intake valve 52 and exhaust valve 54. In some embodiments, combustion chamber 30 may include two or more intake valves and/or two or more exhaust valves.

Fuel injector 66 is shown coupled directly to combustion chamber 30 for injecting fuel directly therein in proportion to the pulse width of signal FPW received from controller 12 via electronic driver 68. In this manner, fuel injector 66 provides what is known as direct injection of fuel into combustion chamber 30. The fuel injector may be mounted in the side of the combustion chamber or in the top of the combustion chamber, for example. Fuel may be delivered to fuel injector 66 by fuel system 2. Fuel system 2 may include various components, including a fuel/water separator and a water reservoir (shown in FIG. 2). While fuel from fuel system 2 may travel to the engine via fuel injector 66, water may travel from the water reservoir in fuel system 2 to the engine via the EGR system. Fuel system 2 components will be presented in more detail at FIG. 2.

The injection timing of fuel from the fuel injector (or injectors) may be adjusted, depending on engine operating conditions. For example, fuel injection timing may be retarded or advanced from controller pre-set values in order to maintain desired engine torque and performance.

Intake manifold 46 may include a throttle 62, positioned upstream of an EGR passage 78 and intake manifold 46 junction, having a throttle plate 64. In this particular example, the position of throttle plate 64 may be varied by controller 12 via a signal provided to an electric motor or actuator included with throttle 62, a configuration that is commonly referred to as electronic throttle control (ETC). In this manner, throttle 62 may be operated to vary the intake air provided to combustion chamber 30 among other engine cylinders. The position of throttle plate 64 may be provided to controller 12 by throttle position signal TP. Intake passage 42 may include a mass air flow sensor 120 and a manifold air pressure sensor 122 for providing respective signals MAF and MAP to controller 12.

Combustion chamber 30 or one or more other combustion chambers of engine 10 may be operated in a compression ignition mode, without an ignition spark. Further, engine 10 may be turbocharged by a compressor 162 disposed along the intake manifold 46 and a turbine 164 disposed along the exhaust passage 48 upstream of the exhaust after-treatment system 70. Though FIG. 1 shows only one cylinder of a multi-cylinder engine, each cylinder may similarly include its own set of intake/exhaust valves, fuel injector, etc.

Exhaust gas sensor 126 is shown coupled to exhaust passage 48 upstream of an exhaust gas after-treatment system 70. Sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a NOx, HC, or CO sensor. An exhaust gas recirculation (EGR) system 72 may recirculate a desired portion of exhaust gas from exhaust passage 48 to intake manifold 46 via EGR passage 78. The amount of EGR provided to intake manifold 46 may be varied by controller 12 via EGR valve 74. The amount of EGR flow may be influenced by engine load. For example, EGR valve 74 may be closed under conditions of high or very low (e.g., zero) engine load.

Under some conditions, the EGR system may be used to regulate the temperature of the air and fuel mixture within the combustion chamber. EGR may reduce combustion chamber temperatures and reduce the amount of NOx generated. Thus, EGR settings (e.g., flow, amount, temperature) may be set based on a desired engine dilution level in order to reduce NOx emissions. FIG. 1 shows a high pressure EGR system where EGR is routed from upstream of a turbine of a turbocharger to downstream of a compressor of a turbocharger. In other embodiments, the engine may additionally or alternatively include a low pressure EGR system where EGR is routed from downstream of a turbine of a turbocharger to upstream of a compressor of the turbocharger.

While EGR may help to reduce NOx emissions, increased EGR may also negatively affect engine performance. In some situations, excessive EGR may cause engine misfires and/or partial burn events resulting in the formation of excess soot in the combustion chamber. Excess EGR may also make combustion less efficient, resulting in degraded fuel economy and excess EGR may introduce other contaminants into the engine. Therefore, adjustments to engine actuators (described further below) in response to EGR flow may be used to maintain desired engine performance. For example, during increased EGR, a throttle opening may be decreased to maintain a desired torque.

Introducing water from fuel system 2 into EGR system 72 may affect EGR and engine performance. In one example, adding water to EGR may cause more engine dilution than was requested, degrading engine performance. Thus, modification to EGR system control may be needed when water is introduced. For example, during water introduction, the amount of EGR may be reduced. Controller 12 may also adjust engine actuators during water introduction. Actuator adjustments may include adjusting injection timing and/or adjusting throttle opening. For example, injection timing may be advanced in response to water introduction to the EGR.

The exhaust gas after-treatment system 70 may include a plurality of emission control devices, each of which may carry out an exothermic reaction with excess oxygen present in the exhaust during selected conditions (e.g., selected temperatures). For example, the exhaust gas after-treatment system 70 may include a diesel oxidation catalyst (DOC) 80 disposed along exhaust passage 48 downstream of turbine 164. The diesel oxidation catalyst may be configured to oxidize HC and CO in the exhaust gas. A selective catalytic reduction catalyst (SCR) catalyst 82 may be disposed along the exhaust gas conduit downstream of DOC 80. The SCR catalyst may be configured to reduce NOx in the exhaust gas to nitrogen and water. A urea sprayer 84 (or any suitable SCR reductant source, such as an ammonia source) may be disposed upstream of SCR catalyst 82 and downstream of DOC 80. A diesel particulate filter (DPF) 86 may be disposed along the exhaust conduit downstream of SCR catalyst 82. The DPF may be configured to remove diesel particulate matter (or soot) from the exhaust gas.

Temperature sensors 88, 90, 92, and 94 may be disposed at points along the exhaust gas conduit both upstream and downstream of each after-treatment device in the after-treatment system 70. The temperature sensors may be used to determine, for example, when to regenerate DPF 86. Further, an oxygen sensor 96 (e.g., an UEGO sensor) may be disposed downstream of the exhaust after-treatment system 70 for measuring an exhaust gas air/fuel ratio. It should be understood that exhaust after-treatment system 70 may include a plurality of after-treatment device configurations not shown in FIG. 1. In one example, the exhaust after-treatment system may only include a DOC. In another example, the exhaust after-treatment system may include a DOC followed downstream by a DPF. In another example, the exhaust after-treatment system may include a DOC followed downstream by a DPF then and SCR. In still another example, SCR catalyst 82 shown in FIG. 1 may be replaced with a lean NOx trap (LNT). Further, the order or arrangement of the different catalysts and filters in the exhaust after-treatment system may vary. The number of temperature sensors disposed within the exhaust after-treatment system may vary according to the application and/or configuration. Though the oxygen sensor (96) is shown in FIG. 1 at a point located downstream of exhaust after-treatment system 70, it may be located upstream of any of the bricks in the after-treatment system 70, in which case it can only monitor the catalyst bricks upstream of it.

Controller 12 is shown in FIG. 1 as a microcomputer, including microprocessor unit 102, input/output ports 104, an electronic storage medium for executable programs and calibration values shown as read only memory chip 106 in this particular example, random access memory 108, keep alive memory 110, and a data bus. Controller 12 may receive various signals from sensors coupled to engine 10, in addition to those signals previously discussed, including measurement of inducted mass air flow (MAF) from mass air flow sensor 120; engine coolant temperature (ECT) from temperature sensor 112 coupled to cooling sleeve 114; a profile ignition pickup signal (PIP) from Hall effect sensor 118 (or other type) coupled to crankshaft 40; throttle position (TP) from a throttle position sensor; boost pressure (Boost) from boost pressure sensor 123; and absolute manifold pressure signal, MAP, from sensor 122. Engine speed signal, RPM, may be generated by controller 12 from signal PIP. Manifold pressure signal MAP from a manifold pressure sensor may be used to provide an indication of vacuum, or pressure, in the intake manifold. Additionally, controller 12 may communicate with a cluster display device 140, for example to alert the driver of faults in the engine or exhaust after-treatment system.

Furthermore, controller 12 may communicate with various actuators, which may include engine actuators such as fuel injectors, an electronically controlled intake air throttle plate, camshafts, etc. Engine actuators may be adjusted based on various engine controls, including control of the EGR system. For example, engine actuators such as the throttle plate may need to be adjusted when the amount of EGR is altered (via changing the position of EGR valve 74). Further details related to example EGR system control will be described below in reference to FIGS. 4-6. In some examples, storage medium read only memory chip 106 may be programmed with computer readable data representing instructions executable by microprocessor unit 102 for performing the methods described below as well as other variants that are anticipated but not specifically listed.

FIG. 2 shows a schematic 200 of a detailed embodiment of the fuel system 2 previously introduced in FIG. 1. Diesel fuel may be supplied to fuel tank 202. Fuel tank sensor 217 may measure a fuel amount in fuel tank 202 and transmit the measured fuel amount to controller 12. Diesel fuel travels from fuel tank 202 to a fuel/water separator 204 where water-based fluid may be separated from the diesel fuel. The separated fuel may then exit the fuel/water separator and travel to supply pump 206. The fuel may then pass through another filter 208. The order of filtering and water separating may be interchanged. Filtered fuel is then pumped via injection pump 210 into a fuel rail 224. Fuel rail 224 may distribute fuel to a set of fuel injectors 212. Four fuel injectors are shown in FIG. 2; however, there may be any number depending on the number of cylinders in the vehicle. A fuel injector 66 may inject fuel into a combustion chamber 30, as shown in FIG. 1.

Returning to fuel/water separator 204, the separated water-based fluid (herein referred to as water) may drain into a water collection reservoir 226 at the bottom of the fuel/water separator. Fuel/water separator 204 may further include a water-in-fuel (WIF) sensor 216 to detect the amount of water in the water collection reservoir 226. WIF sensor 216 may be any suitable sensor (e.g., optical, thermal, or electric conductivity, etc.) and may be, for example, coupled to an inner surface of water collection reservoir 226. In some embodiments, WIF sensor 216 may be positioned at a threshold level that corresponds to a pre-determined threshold volume of water that has been separated from the fuel system. The threshold level may be pre-determined so as to correspond to, for example, a volume of fluid beyond which the probability of introducing water into the high pressure fuel system on the engine (with the fuel) is significantly increased. As such, if water is introduced with the fuel, fuel system degradation may result. Thus, WIF sensor 216 can indicate when a threshold level of water has accumulated in the reservoir, so that an engine controller can take actions to reduce degradation to the fuel system and/or engine. For example, when the sensor detects that a threshold level of water has been exceeded, a raw voltage signal may be produced by the sensor indicating a water-in-fuel condition. This signal may be received by controller 12, triggering the opening of valve 220 and subsequent drainage of water from water collection reservoir 226.

In some embodiments, a water reservoir 214 may be coupled to fuel/water separator 204. Water reservoir 214 may be larger than water collection reservoir 226, allowing for additional water accumulation. Thus, this second reservoir may allow for more flexibility in reservoir volume thresholds for water introduction into the EGR system. Flow of water from the water collection reservoir 226 to the water reservoir 214 may be controlled by controller 12 via valve 220. In alternate embodiments of fuel system 2, water may drain directly from the water collection reservoir 226 to EGR system 72 via valve 220. Water reservoir 214 may also include a water reservoir sensor 218 to measure the amount of water in the reservoir. As for the WIF sensor 216 described above, water reservoir sensor 218 may be any suitable sensor and may be coupled to the inner surface of water reservoir 214. Water reservoir sensor 218 may provide controller 12 with information on water level and/or water volume. When a threshold water level or volume, is reached, a base water-in-fuel flag may be set to ON. The threshold water level or volume may correspond to a water volume at which a risk for exceeding water reservoir capacity is increased. When the base water-in-fuel flag is ON, a signal may be sent to controller 12 to indicate that water should be drained from the water reservoir 214.

Water may be drained from the water reservoir 214 either manually via drain valve 228 when the engine is off, or automatically via water reservoir valve 222 and introduced into the EGR system 72. Manually draining the water reservoir 214 is not possible when the engine is running For example, controller 12 may open water reservoir valve 222 to allow drainage of water into the inlet of the EGR when additional engine operating conditions are satisfied. Introducing water from the water reservoir 214 into EGR system 72 via water reservoir valve 222 may allow EGR flow to be reduced, while still controlling NOx emission levels. Water introduced into the EGR system 72 may also absorb heat and reduce combustion temperatures. As discussed above, while EGR may decrease NOx emissions, it may also negatively influence engine performance and add contaminants to the intake air. Accordingly, the addition of water to EGR may cause more engine dilution than was requested, degrading engine performance. Thus, it may be advantageous to add water from the fuel system to the EGR system selectively under conditions when EGR may be correspondingly reduced. For example, if EGR flow is above a minimum threshold EGR flow, water may be introduced. Methods for controlling water-in-fuel responsive to a refueling event are described further below in reference to FIGS. 3, 4A, and 4B.

In this manner, a vehicle may comprise an engine, a fuel/water separator, a water-in-fuel sensor, and a controller, with instructions stored in memory executable to determine a water-in-fuel content responsive to a refueling event, and generate a water-in-fuel indication responsive to the water-in-fuel content increasing above a threshold amount within a threshold time after the refueling event. The controller may further comprise instructions executable to measure a water volume collected from the fuel/water separator with the water-in-fuel sensor. The vehicle may further comprise a water reservoir downstream from the fuel/water separator, wherein the water-in-fuel sensor is positioned at the water reservoir. Furthermore, the water volume collected from the fuel/water separator may comprise water collected in the water reservoir.

Figure 3:
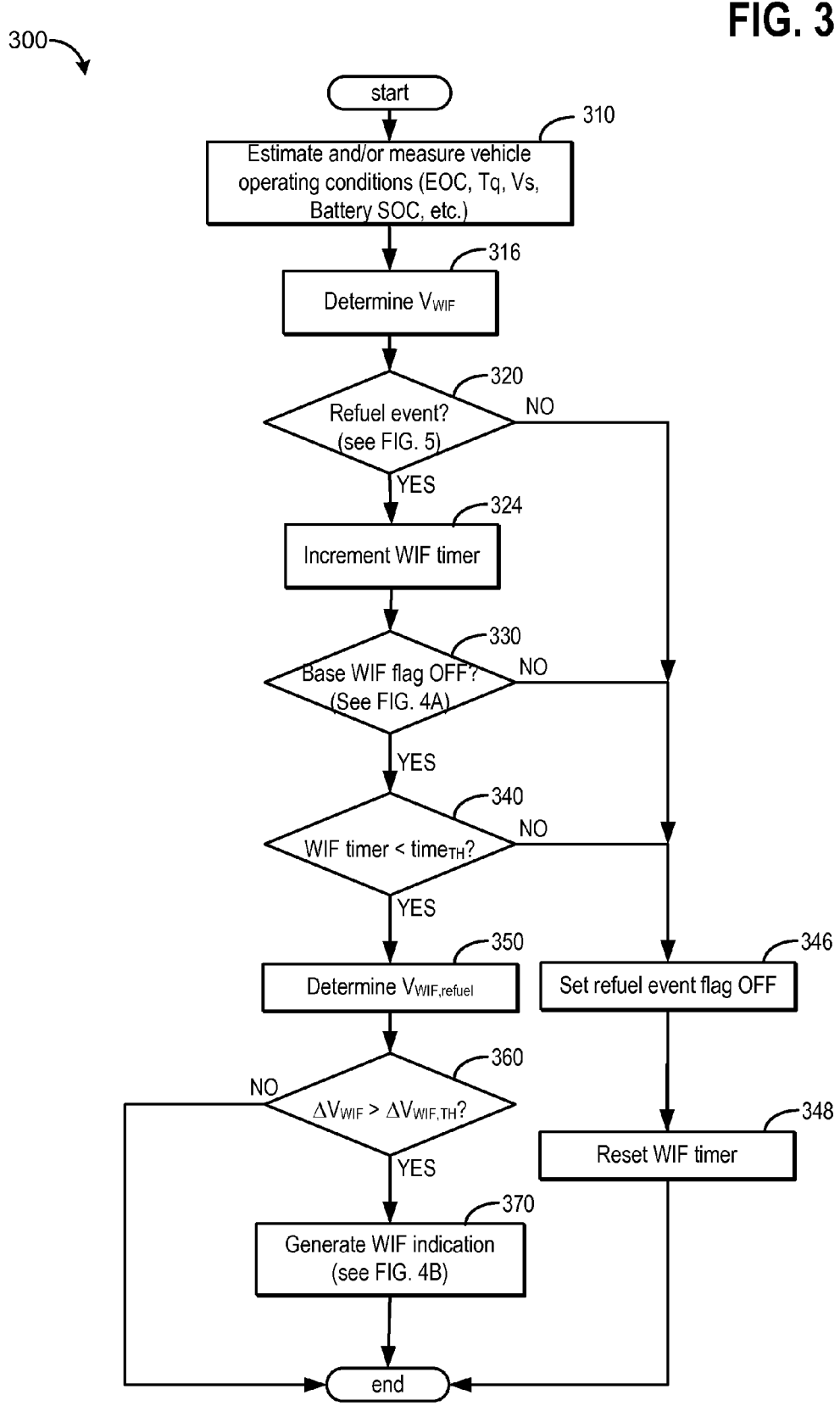
FIGS. 3, 4A, 4B, and 5 show high level flow charts of an example method for generating a water-in-fuel indication responsive to a refueling event.

Turning now to FIG. 3, it illustrates a flow chart for an example method 300 of generating a water-in-fuel indication following a refueling condition. Method 300 begins at 310 where it estimates and/or measures vehicle operating conditions such as engine on condition (EOC) torque, vehicle speed, battery state-of-charge (SOC), and the like. Next, at 316, method 300 determines a water-in-fuel volume, $V_{WIF}$. The water-in-fuel volume, $V_{WIF}$, may be measured using WIF sensor 216 and/or water reservoir sensor 218 and may correspond to a water volume in water reservoir 214 and/or water collection reservoir 226 just prior to a refueling event. At 320, method 300 determines if a refuel event has occurred.

Figure 5:
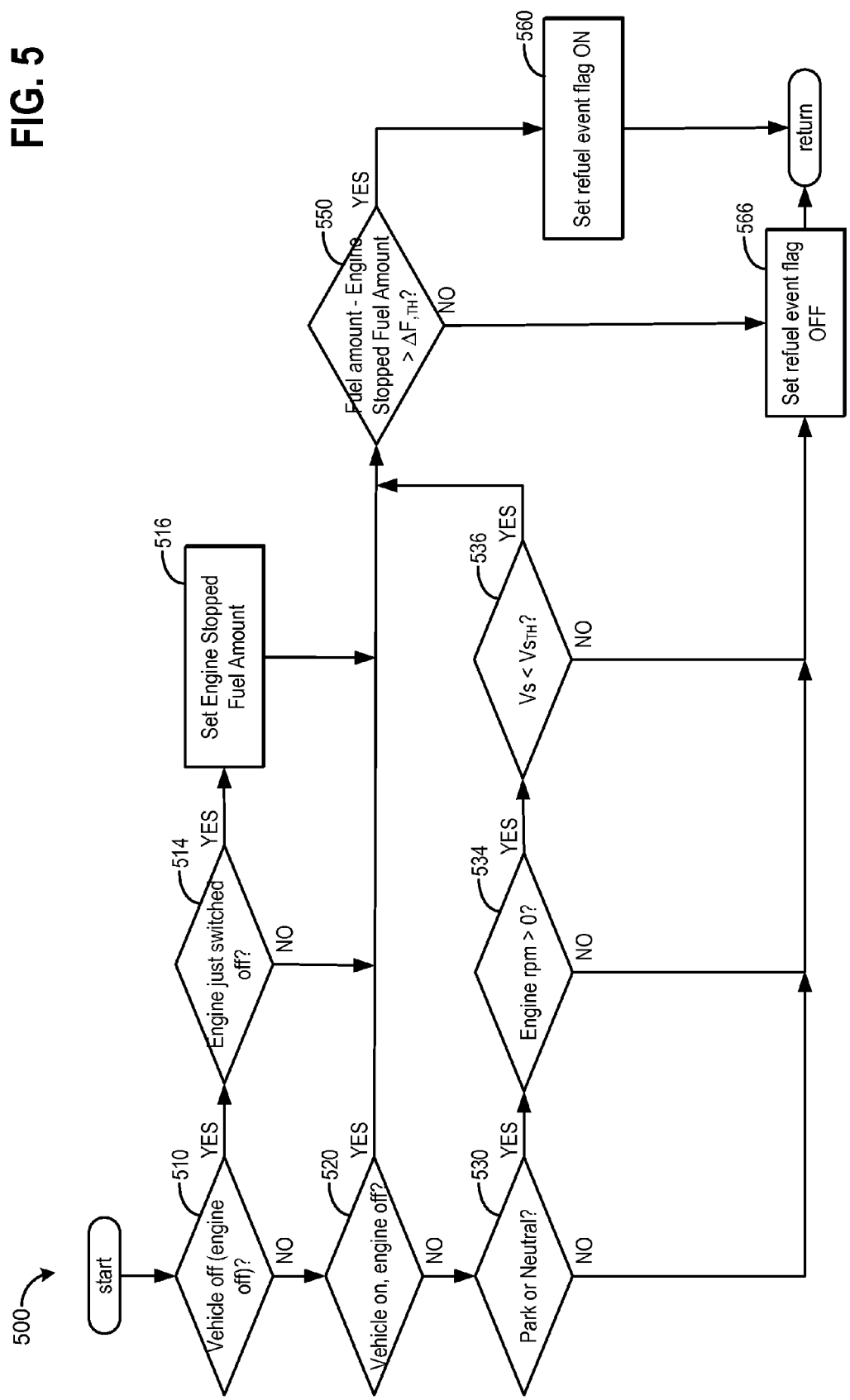
Figure 6:
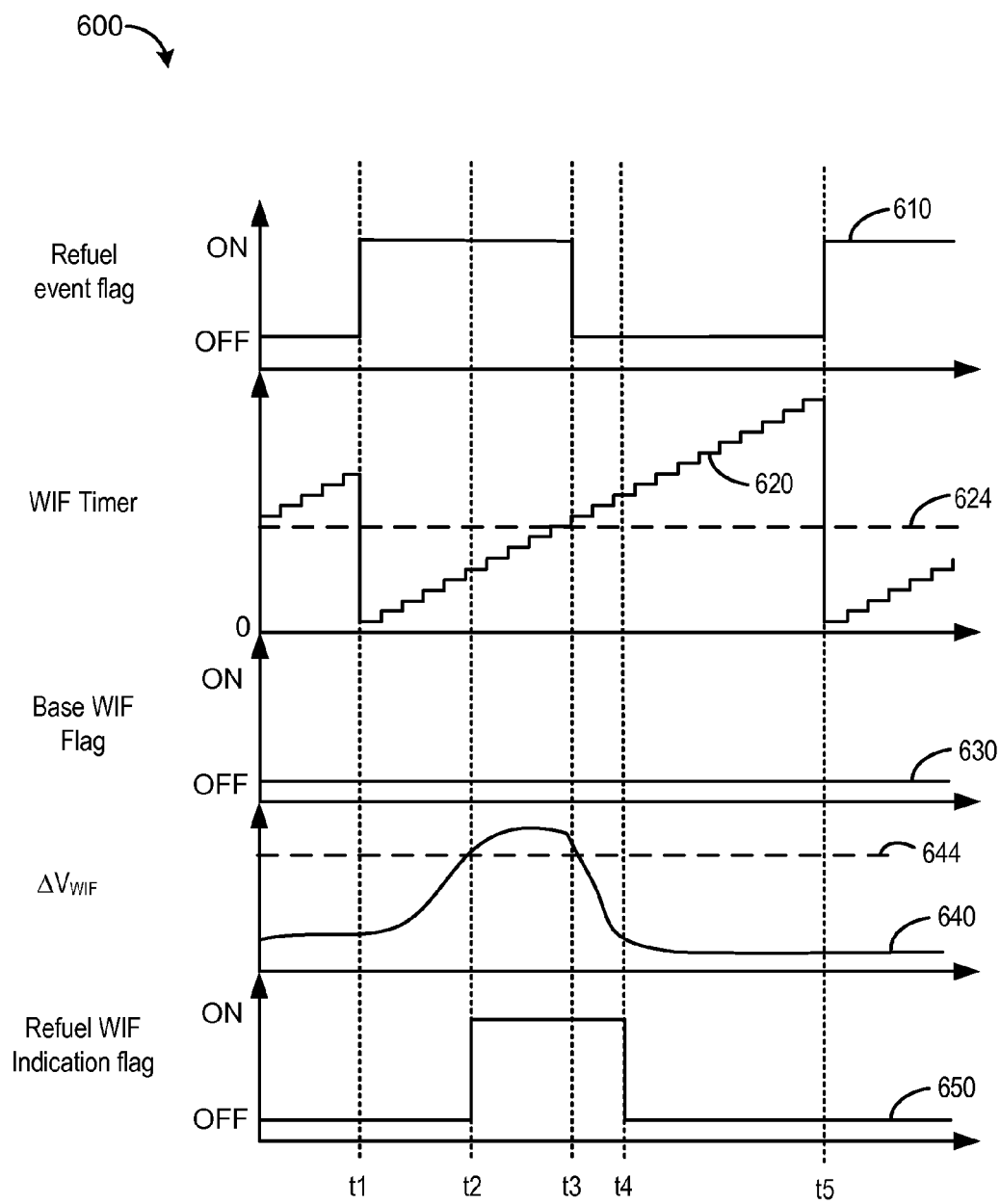
FIG. 6 show flow an example timeline for generating a water-in-fuel indication responsive to a refueling event.

Turning to FIG. 5, it illustrates a flow chart for an example method 500 for determining if a refueling condition is satisfied. Refueling can occur (and thus the refueling condition may be satisfied) when the engine is off (e.g., key on, engine off; or key off, engine off; or vehicle on, engine off; or vehicle off, engine off) or the engine is running Method 500 begins at 510 where it determines if a vehicle off (e.g., engine off) condition is satisfied. If a vehicle off condition is satisfied, method 500 determines if the engine has just been switched off at 514. For example, an EOC status may be stored in memory of controller 12. When an EOC status is switched from engine on (e.g., engine running) to engine off, method 500 may determine that the engine has just been switched off. If the engine has just been switched off, method 500 continues at 516 where an engine stopped fuel amount is set. As an example, the engine stopped fuel amount may be set within a second threshold time of stopping the engine. In one case, the second threshold time may be 20 seconds or another suitable time interval so that the Engine Stopped Fuel Amount is set in a timely fashion after stopping the engine and so that an accurate Engine Stopped Fuel Amount can be recorded prior to a start of a refueling event. The engine stopped fuel amount may be stored in memory (e.g., RAM 108 or KAM 110) of controller 12.

Returning to 510, if a vehicle off condition is not satisfied, method 500 continues at 520 where it determines if a vehicle on, engine off status is satisfied. The vehicle on, engine off status may be satisfied when the ignition button is depressed or a key is turned to the ignition ON position (e.g., so that auxiliary electrical devices are operative), but the engine remains off. If the vehicle on, engine off status is not satisfied, the engine is running, and method 500 proceeds at 530 where it determines if the transmission is set to Park or Neutral. If the transmission is set to Park or Neutral, method 500 continues at 534 where it determines if the engine rpm is greater than zero. If the engine rpm is greater than zero, then method 500 continues at 536 where it determines if the vehicle speed is less than a threshold vehicle speed, $Vs_{TH}$. As an example, $Vs_{TH}$ may be 2 km/h. If at 530 the transmission is not in Park or Neutral, or if $Vs>Vs_{TH}$ at 536, then the vehicle may be in motion and method 500 continues at 566 where a refueling condition is not satisfied and a refuel event flag is set OFF. If the Engine rpm is not greater than zero at 534 when the engine is running, then the engine may be malfunctioning, and method 500 continues at 566 where a refueling condition is not satisfied.

Method 500 proceeds to 550 if a vehicle on, engine off status is satisfied at 520, if the engine has not just been switched off at 514, if $Vs<Vs_{TH}$ at 536, or after setting the Engine Stopped Fuel Amount at 516. At 550, method 500 determines if an increase in fuel amount relative to the Engine Stopped Fuel Amount is greater than a threshold fuel increase, $\Delta F_{TH}$. In one example, $\Delta F_{TH}$ may be a relative fuel increase. For example, if the amount of fuel in the fuel tank 202 measured by fuel tank sensor 217 increases beyond a threshold percentage increase of the rated fuel tank capacity, then a refueling condition may be satisfied and a refuel event flag is set ON at 560. In this case, $\Delta F_{TH}$ may comprise 3% or 6% of the rated fuel tank capacity. In another example, $\Delta F_{TH}$ may correspond to an absolute fuel increase. For example, if the amount of fuel in the fuel tank 202 measured by fuel tank sensor 217 increases beyond a threshold fuel amount above the Engine Stopped Fuel Amount, then a refueling condition may be satisfied and a refuel event flag is set ON at 560. If the increase in fuel amount relative to the Engine Stopped Fuel Amount is not greater than $\Delta F_{TH}$, then a refueling condition is not satisfied and a refuel event flag is set OFF at 566. After 560 and 566, method 500 returns to method 300 at 320.

Method 500 is an example method of detecting a refueling event. Other known methods of detecting a refueling event may be used. For example, a method for detecting a refueling event may comprise monitoring a fuel tank pressure, and indicating a refueling event when an increase or rate of increase in the fuel tank pressure greater than a threshold increase or a threshold rate of increase, respectively. The method may further comprise setting the refuel event flag ON when a refuel event is detected, and setting a refuel event flag OFF when a refuel event is not detected. Other methods of detecting a refueling event may be utilized.

Figure 4B:
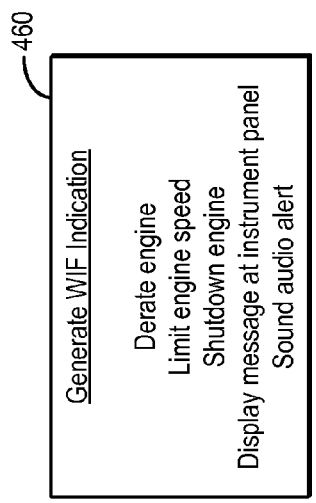
Figure 4A:
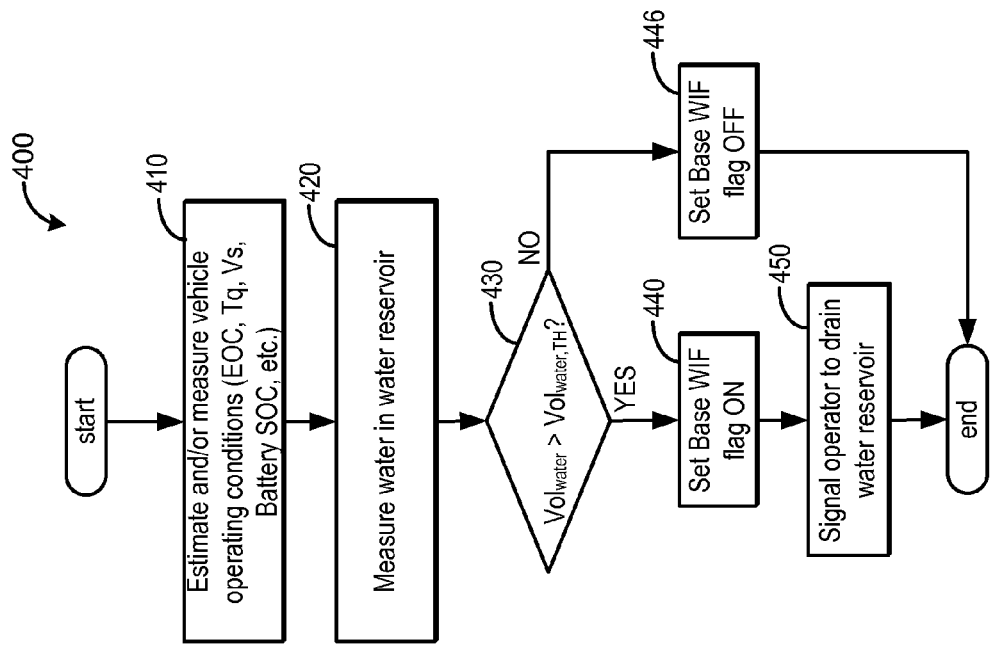

If a refueling condition is satisfied at 320, method 300 increments a WIF timer at 324. After 324, method 300 continues at 330 where it determines if a Base WIF flag is off. The Base WIF flag status indicates if a water volume, $Vol_{water}$, in the water collection reservoir 226 or water reservoir 214 measured by WIF sensor 216 or water reservoir sensor 218 respectively is greater than a threshold volume, $Vol_{water,TH}$. FIG. 4A illustrates an example method 400 for determining the Base WIF flag status.

Method 400 begins at 410 where it estimates and/or measures vehicle operating conditions such as engine on conditions, torque, vehicle speed, battery SOC, and the like. At 420, method measures the water volume in the water reservoir 214. WIF sensors 216 and/or water reservoir sensor 218 may account for inherent slosh in the water reservoir 214 due to motion of the vehicle to provide an estimated measurement for the water volume. At 430, method 400 determines if the measured $Vol_{water}$ is greater than a threshold water volume, $Vol_{water,TH}$. The threshold water volume may correspond to a water reservoir volume above which a risk of passing water to the engine injection system is substantially increased and a signal is sent to the vehicle operator to have the water reservoir drained. If $Vol_{water}>Vol_{water,TH}$, then method 400 continues at 440 where the Base WIF flag is set to ON. If $Vol_{water}$ is not greater than $Vol_{water,TH}$, then method 400 continues at 446 where the Base WIF flag is set to OFF. Method 400 is executed irrespective of whether a refueling event has occurred, and irrespective of whether the vehicle is in motion or stationary. Furthermore, method 400 is suitable for detecting a gradual increase in water reservoir volume above $Vol_{water,TH}$. After 440, method 400 signals the operator to drain the water reservoir at 450. Signaling the operator may comprise one or more of sending an audible warning, generating a visible message on the vehicle instrument panel, and the like. After 450 and 446, method 400 ends.

Returning to method 300 at 330, if the Base WIF flag is OFF, then method 300 continues at 340 where it determines if a WIF timer is less than a first threshold time, $time_{TH}$. The first threshold time may correspond to a short interval following completion of a refueling event. For example, $time_{TH}$ may correspond to a time interval long enough to allow the fuel/water separator 204 to coalesce and separate any water in the fuel into the water collection reservoir 226 and water reservoir 214, but short enough to reduce the risk of accumulating a volume of water exceeding the capacity of the water reservoir 214. In one example, $time_{TH}$ may be one minute or 30 seconds. The higher density water as compared to fuel (e.g., diesel fuel, gasoline) can facilitate efficient separation of the water from the fuel in the fuel/water separator 204 into the water collection reservoir 226 and the water reservoir 214. First threshold time, $time_{TH}$, may be a predetermined and calibratable time, depending on the fuel type, fuel/water separator 204 volume and fluid flow dynamics, water collection reservoir 226 volume, water reservoir 214 volume, measurement dynamics of WIF sensor 216 and water reservoir sensor 218, and the like. Furthermore time$_{TH}$ may correspond to a time interval following completion of a refueling event prior to when a vehicle operator typically resumes driving (e.g., vehicle is no longer stationary after refueling). Further still, during the first threshold time, vehicle operation may be limited to reduce a risk of degradation to engine components due to water-in-fuel content. For example, vehicle speed may be limited below a threshold vehicle speed, engine rpm may be limited, and engine power may be limited. However, during the first threshold time, the vehicle may be ON, the engine may be running Furthermore, auxiliary devices may be powered, such that, for example, if water-in-fuel content is high (e.g. see 350, 360, 370 in FIG. 3) following completion of refueling a Refuel WIF indication Flag may be set ON and a refuel WIF indication may be generated to notify the operator accordingly.

If WIF timer is less than time$_{TH}$, method 300 continues at 350 where it determines the current WIF content $V_{WIF,refuel}$, for example, employing the WIF sensor 216 and/or the water reservoir sensor 218. In contrast to the measurement of Vol$_{water}$ in method 400, $V_{WIF, refuel}$ is measured at 350 with reduced inherent slosh, since the vehicle may be stationary or near stationary (e.g., Vs<Vs$_{TH}$). In particular, method 300 at 350 may be suited to measuring large changes in water volume (e.g., a large slug of water) quickly (e.g., within time$_{TH}$), and the measurement signal may be a steady (e.g., solid) signal generated by the water volume in the water reservoir 214 and/or water collection reservoir 226. In this manner WIF sensor 216 and/or water reservoir sensor 218 may each correspond to two sensors, a first sensor being suited to estimating a water volume in the presence of slosh, and a second sensor suited to measuring steady changes in volume over a short interval of time (e.g., time$_{TH}$).

At 360, method 300 determines the change in water volume relative to the water-in-fuel content, $V_{WIF}$, measured just prior to the refueling event. The change in water volume, $\Delta V_{WIF}$, may correspond to an absolute or relative difference between $V_{WIF, refuel}$ and $V_{WIF}$. At 360 method 300 further determines if the change in water volume $\Delta V_{WIF}$ is less than a threshold change in water volume, $\Delta V_{WIF,TH}$. The threshold change in water volume, $\Delta V_{WIF,TH}$, may correspond to a non-zero change in water volume indicative of a high water-in-fuel content. For example, if $\Delta V_{WIF}$ is greater than $\Delta V_{WIF,TH}$, then the fuel tank may have been refueled with high water-in-fuel content diesel or gasoline, and a risk of exceeding a water reservoir 214 capacity following a refueling event may be substantially increased.

For the case of large refueling amounts (e.g. filling an empty tank), the change in water volume, $\Delta V_{WIF}$, may increase at a faster rate, and $\Delta V_{WIF,TH}$ may be reached in a shorter time interval following a refueling event as compared to when the refueling amount is smaller. Accordingly method 300 detects and generates a refuel WIF indication more promptly when the risk of exceeding a water reservoir capacity is increased. If $\Delta V_{WIF}$ is less than $\Delta V_{WIF,TH}$, then method 300 ends. If $\Delta V_{WIF}$ is greater than $\Delta V_{WIF,TH}$, method 300 continues at 370, where it generates a refuel WIF indication to the vehicle operator. FIG. 4B illustrates example refuel WIF indications that may be generated. For instance, the engine may be derated and/or the engine speed may be limited in order to limit engine power and to reduce a risk of damage to the engine system due to encroachment of water. Furthermore, the engine may be shut down to reduce the risk of damage to the engine system due to encroachment of water. Further still, a message may be displayed at the instrument panel and an audio alarm may be generated to warn the vehicle operator of a high WIF content following a refueling event. In some cases, one or more refuel WIF indications may be generated, and the number and type of refuel WIF indication generated may correspond to the amount of water-in-fuel content detected and the severity of the risk of engine damage. For example, if a vehicle fuel tank has been filled from a near empty tank with high water-in-fuel content containing diesel, and a risk of exceeding the water reservoir capacity is high, the engine may be shut down, and visual and audio alarms may be generated to warn the vehicle operator to drain the water reservoir. As discussed previously with reference to FIGS. 1 and 2, the water reservoir may be manually drained and/or automatically drained to the EGR system under suitable conditions. After 370, method 300 ends If at 320 a refuel event is not detected, method 300 bypasses the detection of water-in-fuel content responsive to a refueling event, sets the refuel event flag OFF at 346, resets the WIF timer at 348, and ends. Furthermore, if at 330 the Base WIF flag is ON, then the vehicle operator has already been signaled to drain the water reservoir 214 at 450 of method 400, and method 300 bypasses the detection of water-in-fuel content responsive to a refueling event, sets the refuel event flag OFF at 346, resets the WIF timer at 348, and ends.

If at 340, the WIF timer is greater than time$_{TH}$, then an increase in water-in-fuel content following a refueling condition is not detected within a first threshold time (e.g., water-in-fuel content from the refueling event is low), and method 300 bypasses the detection of water-in-fuel content responsive to a refueling event, sets the refuel event flag OFF at 346, and ends.

In this manner, a method for an engine may comprise generating a water-in-fuel indication responsive to a water-in-fuel content increasing more than a threshold amount within a first predetermined threshold duration of a refueling event. The method may further comprise limiting an engine speed in response to the water-in-fuel indication, and shutting down the engine in response to the water-in-fuel indication. The water-in-fuel content may be determined based on a change in water volume collected from a fuel/water separator after the refueling event within the first threshold time, without any other refueling events therebetween. Furthermore, generating the water-in-fuel indication comprises generating an audio alert, and the refueling event comprises an increase in a fuel amount beyond a threshold fuel increase. The method may further comprise determining the water-in-fuel content responsive to a vehicle on, engine off, refueling event, and determining the water-in-fuel content responsive to an engine running refueling event, wherein the engine running refueling event comprises one or more of a transmission in park, a transmission in neutral, and an engine rpm greater than zero.

In another embodiment, a method may comprise responsive to a refueling condition and following completion of refueling, measuring a change in a water-in-fuel content, and generating a water-in-fuel operator indication if the change in the water-in-fuel content is greater than a non-zero threshold amount. The method may further comprise generating the water-in-fuel indication if the change in the water-in-fuel content is greater than the threshold amount within a first threshold time following the refueling condition. The refueling condition may comprise a vehicle on engine off refueling condition, and/or an engine running refueling condition, and/or one or more of a vehicle transmission in park, a vehicle transmission in neutral, and an engine rpm greater than zero. Furthermore, generating the water-in-fuel operator indication may comprise derating the engine, and may the refueling condition may comprise an increase in a fuel amount above an engine stopped fuel amount beyond a threshold fuel amount, the engine stopped fuel amount determined just prior to the refueling condition. Further still, measuring the change in the water fuel content may comprise measuring an increase in water volume collected from a fuel/water separator within the first threshold time.

Turning now to FIG. 6, it illustrates a timeline 600 for an example method of generating a refuel WIF indication responsive to a refueling event. Timeline 600 includes trend lines for refuel event flag status 610, WIF timer 620, Base WIF flag status 630, $DV_{WIF}$ 640, and refuel WIF indication flag 650. Additionally, timeline 600 includes the first threshold time 624, $time_{TH}$, and the threshold change in water volume 644, $\Delta V_{WIF,TH}$, indicated by dashed lines.

Prior to a time, t1, a refuel event flag is OFF, and WIF timer increments gradually with time. Furthermore, Base WIF Flag is OFF, indicating that $Vol_{water}$ is less than $Vol_{water,TH}$ (e.g., water-in-fuel content is low), and $\Delta V_{WIF}$ is also low. Further still, refuel WIF indication flag is OFF. At t1, a refuel event is detected, for example, when a fuel amount exceeds an engine stopped fuel amount by a threshold fuel amount, $\Delta F_{TH}$ during a condition when the EOC comprises vehicle off (engine off); vehicle on, engine off; or the engine is running but in Park or Neutral wherein the engine rpm is greater than 0 and the vehicle speed is less than $Vs_{TH}$. In response to the refuel event detection, the refuel event flag is set ON, and WIF timer is reset to 0. During the refueling event, fuel with a high water-in-fuel content was introduced into the fuel tank 202. As such, $\Delta V_{WIF}$ rapidly begins increasing between t1 and t2, as WIF timer is incremented following the refueling event.

At t2, $\Delta V_{WIF}$ exceeds $\Delta V_{WIF,TH}$ 644. Because the time elapsed since the refuel event (e.g., t2-t1) is less than $time_{TH}$, indicated by the WIF timer 620 being less than first threshold time 624, a refuel WIF indication flag 650 is set to ON at t2. Setting the refuel WIF indication flag ON generates one or more indicators notifying the vehicle operator of the increased risk of exceeding the water reservoir capacity following the refueling condition. For example, a warning message may be generated at the instrument panel along with an audible alarm. Furthermore, the engine speed may be limited, or the engine may be shut down. The refuel WIF indication may be sustained until the water reservoir 214 is drained.

At t3, the WIF timer surpasses $time_{TH}$ and the refuel event flag 610 is set OFF. Also during the period between t3 and t4, the water reservoir is drained. Thus, at t4, the refuel WIF indication flag is set OFF. WIF timer 620 continues to be gradually incremented until a time t5, when another refueling event is detected.

At t6, the refuel event flag is set ON, and WIF timer is reset to 0. In this case, the fuel introduced into fuel tank 202 does not have appreciable water-in-fuel content, and the change in water volume, $\Delta V_{WIF}$, does not increase. Accordingly, a refuel WIF indication is not generated.

Note that the example control and estimation routines included herein can be used with various engine and/or vehicle system configurations. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for an engine, comprising:
incrementing time upon completion of a refueling event;
setting a first threshold time, wherein the first threshold time is a predetermined and calibratable time interval following the refueling event; and
generating a water-in-fuel indication responsive to a water-in-fuel content increasing more than a threshold amount when the incremented time is within the first threshold time of the refueling event.

2. The method of claim 1, further comprising limiting an engine speed in response to the water-in-fuel indication.

3. The method of claim 1, further comprising shutting down the engine in response to the water-in-fuel indication.

4. The method of claim 1, wherein the water-in-fuel content is determined based on a change in water volume collected from a fuel/water separator after the refueling event within the first threshold time, without any other refueling events therebetween.

5. The method of claim 1, wherein generating the water-in-fuel indication comprises generating an audio alert.

6. The method of claim 1, further comprising determining the water-in-fuel content responsive to a vehicle on, engine off, refueling event, wherein the refueling event comprises an increase in a fuel amount beyond a threshold fuel increase.

7. The method of claim 1, further comprising determining the water-in-fuel content responsive to an engine running refueling event, wherein the engine running refueling event comprises one or more of a transmission in park, a transmission in neutral, and an engine rpm greater than zero.

8. A method, comprising:
responsive to a refueling condition and following completion of refueling,
measuring a change in a water-in-fuel content, and
generating a water-in-fuel operator indication if the change in the water-in-fuel content is greater than a non-zero threshold amount, and generating the water-in-fuel operator indication if the change in the water-in-fuel content is greater than the threshold amount within a first threshold time following the refueling condition.

9. The method of claim 8, wherein the refueling condition comprises a vehicle on engine off refueling condition.

10. The method of claim 8, wherein the refueling condition comprises an engine running refueling condition.

11. The method of claim 10, wherein the engine running refueling condition comprises one or more of a vehicle transmission in park, a vehicle transmission in neutral, and an engine rpm greater than zero.

12. The method of claim 8, wherein generating the water-in-fuel operator indication comprises derating an engine.

13. The method of claim 8, wherein the refueling condition comprises an increase in a fuel amount above an engine stopped fuel amount beyond a threshold fuel amount, the engine stopped fuel amount determined just prior to the refueling condition.

14. The method of claim 8, wherein measuring the change in the water-in-fuel content comprises measuring an increase in water volume collected from a fuel/water separator within the first threshold time.

15. A vehicle, comprising,
an engine;
a fuel/water separator;
a water-in-fuel sensor; and
a controller, with instructions stored in memory executable to:
determine a change in water volume collected from the fuel/water separator responsive to a refueling event; and
generate a water-in-fuel indication responsive to the change in water volume being greater than a threshold change in water volume when time elapsed since the refueling event is less than a set threshold time.

16. The vehicle of claim 15, wherein the controller further comprises instructions executable to measure the water volume collected from the fuel/water separator with the water-in-fuel sensor.

17. The vehicle of claim 16, further comprising a water reservoir downstream from the fuel/water separator, wherein the water-in-fuel sensor is positioned at the water reservoir.

18. The vehicle of claim 17, wherein the water volume collected from the fuel/water separator comprises water collected in the water reservoir.

19. The method of claim 4, further comprising at least one of draining a water reservoir containing collected water from the fuel/water separator automatically to an EGR system in response to the water-in-fuel indication and draining the water reservoir manually during engine shutoff in response to the water-in-fuel indication.

20. The method of claim 1, wherein the first threshold time is a time interval that extends from completion of the refueling event to prior to when a vehicle is no longer stationary after refueling, wherein a vehicle speed is limited to below a threshold vehicle speed during the first threshold time, and wherein a timer is reset to zero after the refueling event is detected, and the timer is incremented following the refueling event.

\* \* \* \* \*